US007223565B2

(12) United States Patent
Sims et al.

(10) Patent No.: US 7,223,565 B2
(45) Date of Patent: May 29, 2007

(54) IL-1 ETA DNA AND POLYPEPTIDES

(75) Inventors: John E. Sims, Seattle, WA (US); Blair R. Renshaw, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 340 days.

(21) Appl. No.: 10/843,189

(22) Filed: May 10, 2004

(65) Prior Publication Data

US 2004/0203116 A1    Oct. 14, 2004

Related U.S. Application Data

(63) Continuation of application No. 09/976,472, filed on Oct. 11, 2001, which is a continuation-in-part of application No. PCT/US00/14435, filed on May 25, 2000, now Pat. No. 6,753,166.

(60) Provisional application No. 60/162,331, filed on Oct. 29, 1999, provisional application No. 60/135,758, filed on May 25, 1999.

(51) Int. Cl.
| | |
|---|---|
| *C12N 15/09* | (2006.01) |
| *C12N 15/12* | (2006.01) |
| *C12P 21/02* | (2006.01) |
| *C07K 14/435* | (2006.01) |
| *C07K 14/545* | (2006.01) |

(52) U.S. Cl. .............. 435/69.52; 435/320.1; 435/325; 536/23.5; 530/351; 424/85.2

(58) Field of Classification Search ............... None
See application file for complete search history.

(56) References Cited

U.S. PATENT DOCUMENTS

| 5,945,310 A | 8/1999 | Young et al. ............ 435/69.52 |
| 2002/0068279 A1 | 6/2002 | Burges et al. ................. 435/6 |

FOREIGN PATENT DOCUMENTS

| EP | 879889 A2 | 11/1998 |
| WO | WO01/42305 A1 | 6/2001 |
| WO | WO/0140291 | 6/2001 |

OTHER PUBLICATIONS

Smith, DE, et al., . *Biol. Chem.* 2000, 275(2):11690-1175.
Dinarello, C., *Annals NY Acad Sci* 1998, 856:1-11.

*Primary Examiner*—Prema Mertz
*Assistant Examiner*—Fozi Hamud
(74) *Attorney, Agent, or Firm*—Patricia Anne Perkins

(57) ABSTRACT

The invention is directed to novel, purified and isolated IL-1 eta polypeptides and fragments thereof, the polynucleotides encoding such polypeptides, processes for production of recombinant forms of such polypeptides, antibodies generated against these polypeptides, peptides derived from these polypeptides, and uses thereof.

4 Claims, 3 Drawing Sheets

```
GGCACGAGGT TCCTCCCCAC TCTGTCTTTC TCACCTCTCC TTCACTTTTC

CTAGCCTCCT CACCACCATC TGATCTATCT TGTTCTCTTC ACAAAAGGCT

CTGAAGACAT CATGAACCCA CAACGGGAGG CAGCACCCAA ATCCTATGCT

ATTCGTGATT CTCGACAGAT GGTGTGGGTC CTGAGTGGAA ATTCTTTAAT

AGCAGCTCCT CTTAGCCGCA GCATTAAGCC TGTCACTCTT ATTTAATAG

CCTGTAGAGA CACAGAATTC AGTGACAAGG AAAAGGGTAA TATGGTTTAC

CTGGGAATCA AGGGAAAAGA TCTCTGTCTC TTCTGTGCAG AAATTCAGGG

CAAGCCTACT TTGCAGCTTA AGGAAAAAAA TATCATGGAC CTGTATGTGG

AGAAGAAAGC ACAGAAGCCC TTTCTCTTTT TCCACAATAA AGAAGGCTCC

ACTTCTGTCT TTCAGTCAGT CTCTTACCCT GGCTGGTTCA TAGCCACCTC

CACCACATCA GGACAGCCCA TCTTTCTCAC CAAGGAGAGA GGCATAACTA

ATAACACTAA CTTCTACTTA GATTCTGTGG AATAA (SEQ.ID. NO.:1)
```

Figure 1

```
MNPQREAAPK SYAIRDSRQM VWVLSGNSLI AAPLSRSIKP VTLHLIACRD

TEFSDKEKGN MVYLGIKGKD LCLFCAEIQG KPTLQLKEKN IMDLYVEKKA

QKPFLFFHNK EGSTSVFQSV SYPGWFIATS TTSGQPIFLT KERGITNNTN

FYLDSVE* (SEQ. ID. NO.:2)
```

Figure 2

| Source human tissue | IL-1 ε/η |
|---|---|
| Spleen | − |
| Lymph Node | − |
| Thymus | − |
| Tonsil | a |
| Bone Marrow | a |
| Fetal Liver | − |
| Leukocyte | − |
| Heart | a |
| Brain | − |
| Placenta | a |
| Lung | a |
| Liver | − |
| Skel. Muscle | − |
| Kidney | − |
| Pancreas | − |
| Prostate | − |
| Testis | a |
| Ovary | − |
| Sm. Intestine | − |
| Colon | a |
| fetal brain | |
| NK cells | |
| parathyroid tumor | |
| colon tumor | |
| pool | |

Figure 3

IL-1 ETA DNA AND POLYPEPTIDES

CROSS-REFERENCE TO RELATED APPLICATIONS

This application is a continuation of Ser. No. 09/976,472, filed on Oct. 11, 2001 now U.S. Pat. No. 6,753,166; which is a continuation-in-part of PCT application Ser. No. PCT/US00/14435 filed May 25, 2000; which claims benefit of provisional applications Ser. No. 60/162,331 filed Oct. 29, 1999; and Ser. No. 60/135,758 filed May 25, 1999.

BACKGROUND OF THE INVENTION

1. Field of the Invention

The invention is directed to novel, purified and isolated IL-1 eta polypeptides and fragments thereof, the polynucleotides encoding such polypeptides, processes for production of recombinant forms of such polypeptides, antibodies generated against these polypeptides, fragmented peptides derived from these polypeptides, and uses thereof.

2. Description of Related Art

Interleukin-1 (IL-1) is a member of a large group of cytokines whose primary function is to mediate immune and inflammatory responses. There are seven known IL-1 family members which include IL-1 alpha (IL-1α), IL-1 beta (IL-1β), IL-1 receptor antagonist (IL-1ra), IL-1 delta (IL-1δ), IL-1 epsilon (IL-1ε), IL-1 zeta (IL-1ξ) and IL-18 (previously known as IGIF and sometimes IL-1 gamma). IL-1 that is secreted by macrophages is actually a mixture of mostly IL-1β and some IL-1α (Abbas et al., 1994). IL-1α and IL-1β, which are first produced as 33 kD precursors that lack a signal sequence, are further processed by proteolytic cleavage to produce secreted active forms, each about 17 kD. Additionally, the 33 kD precursor of IL-1α is also active. Both forms of IL-1 are the products of two different genes located on chromosome 2. Although the two forms are less than 30 percent homologous to each other, they both bind to the same receptors and have similar activities.

IL-1ra, a biologically inactive form of IL-1, is structurally homologous to IL-1 and binds to the same receptors. Additionally, IL-1ra is produced with a signal sequence which allows for efficient secretion into the extracellular region where it competitively competes with IL-1 (Abbas et al., 1994).

The IL-1 family of ligands binds to a family of two IL-1 receptors, which are members of the Ig superfamily. IL-1 receptors include the 80 kDa type I receptor (IL-1RI) and a 68 kDa type II receptor (IL-1RII). IL-1 ligands can also bind to a soluble proteolytic fragment of IL-1RII (sIL-1RII) (Colotta et al., 1993).

The major source of IL-1 is the activated macrophage or mononuclear phagocyte. Other cells that produce IL-1 include epithelial and endothelial cells (Abbas et al., 1994). IL-1 secretion from macrophages occurs after the macrophage encounters and ingests gram-negative bacteria. Such bacteria contain lipopolysaccharide (LPS) molecules, also known as endotoxin, in the bacterial cell wall. LPS molecules are the active components that stimulate macrophages to produce tumor necrosis factor (TNF) and IL-1. In this case, IL-1 is produced in response to LPS and TNF production. At low concentrations, LPS stimulates macrophages and activates B-cells and other host responses needed to eliminate the bacterial infection; however, at high concentrations, LPS can cause severe tissue damage, shock, and even death.

The biological functions of IL-1 include activating vascular endothelial cells and lymphocytes, local tissue destruction, and fever (Janeway et al., 1996). At low levels, IL-1 stimulates macrophages and vascular endothelial cells to produce IL-6, upregulates molecules on the surface of vascular endothelial cells to increase leukocyte adhesion, and indirectly activates inflammatory leukocytes by stimulating mononuclear phagocytes and other cells to produce certain chemokines that activate inflammatory leukocytes. Additionally, IL-1 is involved in other inflammatory responses such as induction of prostaglandins, nitric oxide synthetase, and metalloproteinases. These IL-1 functions are crucial during low level microbial infections. However, if the microbial infection escalates, IL-1 acts systemically by inducing fever, stimulating mononuclear phagocytes to produce IL-1 and IL-6, increasing the production of serum proteins from hepatocytes, and activating the coagulation system. Additionally, IL-1 does not cause hemorrhagic necrosis of tumors, suppress bone marrow stem cell division, and IL-1 is lethal to humans at high concentrations.

Given the important function of IL-1, there is a need in the art for additional members of the IL-1 ligand and IL-1 receptor families. In addition, in view of the continuing interest in protein research and the immune system, the discovery, identification, and roles of new proteins (such as the human IL-1 eta of the invention) and their inhibitors, are at the forefront of modern molecular biology and biochemistry. Despite the growing body of knowledge, there is still a need in the art for the identity and function of proteins involved in cellular and immune responses.

SUMMARY OF THE INVENTION

The invention aids in fulfilling these various needs in the art by providing isolated polynucleotides and polypeptides encoded by the polynucleotides for the novel IL-1 family ligand termed "IL-1 eta." Thus, in one aspect, the invention is directed to isolated novel polynucleotide molecules of IL-1 eta comprising the nucleotide residues 112–585 of SEQ ID NO:1 and to the isolated polynucleotide molecules encoding the amino acid sequence of SEQ ID NO:2, as well as polynucleotide molecules complementary to these sequences.

Both single-stranded and double-stranded RNA and DNA molecules are encompassed by the invention, as well as polynucleotide molecules that hybridize to a denatured, double-stranded DNA comprising all or a portion of SEQ ID NO:1 and/or a DNA that encodes the amino acid sequences set forth in SEQ ID NO:2. Also encompassed are isolated polynucleotide molecules that are derived by in vitro mutagenesis of polynucleotide molecules comprising the coding region of SEQ ID NO:1, that are degenerate from polynucleotide molecules comprising the sequence of SEQ ID NO:1, and that are allelic variants of DNA of the invention. The invention also encompasses recombinant vectors that direct the expression of these polynucleotide molecules and host cells transformed or transfected with these vectors.

In addition, the invention encompasses methods of using the DNA noted above to identify DNA encoding proteins having activities associated with IL-1 family ligands and receptors.

In addition, these polynucleotides can be used to identify the human chromosomes with which the polynucleotides are associated. Thus, since the IL-1 eta polynucleotides map to chromosome 2, DNA encoding IL-1 eta polypeptides may be used to identify human chromosome 2. Accordingly, these polynucleotides may also be used to map genes on human chromosome 2; to identify genes associated with certain diseases, syndromes, or other human conditions associated with human chromosome 2; and to study cell signal transduction and the immune system.

The invention also encompasses the use of sense or antisense oligonucleotides from the polynucleotides of SEQ ID NO:1 to inhibit the expression of the respective polynucleotide encoded by the genes of the invention.

The invention also encompasses isolated polypeptides and fragments of IL-1 eta as encoded by these polynucleotide molecules, including soluble polypeptide portions of SEQ ID NO:2. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell proliferation, cell death, cell migration, cell-to-cell interaction, and inflammatory responses. In addition, these polypeptides can be used to identify proteins associated with IL-1 eta ligands.

In addition, the invention includes assays utilizing these polypeptides to screen for potential inhibitors of activity associated with polypeptide counter-structure molecules, and methods of using these polypeptides as therapeutic agents for the treatment of diseases mediated by polypeptide counter-structure molecules. Further, methods of using these polypeptides in the design of inhibitors (e.g., engineered receptors that act as inhibitors) thereof are also an aspect of the invention.

Further encompassed by this invention is the use of the IL-1 eta polynucleotide sequences, predicted amino acid sequences of the polypeptide or fragments thereof, or a combination of the predicted amino acid sequences of the polypeptide and fragments thereof for use in searching an electronic database to aid in the identification of sample polynucleotides and/or proteins.

Isolated polyclonal or monoclonal antibodies that bind to these polypeptides are also encompassed by the invention, in addition the use of these antibodies to aid in purifying the polypeptides of the invention.

BRIEF DESCRIPTION OF THE FIGURES

FIG. 1 presents the nucleotide sequence of IL-1 eta (SEQ ID NO:1).

FIG. 2 presents the amino acid sequence of IL-1 eta (SEQ ID NO:2).

FIG. 3 is a table summarizing expression data of IL-1 eta. "-" indicates that the mRNA was looked for but not found; a blank space indicates that the analysis was not done for that particular gene/RNA combination.

DETAILED DESCRIPTION OF THE INVENTION

The polynucleotide molecules encompassed in the invention include the following nucleotide sequence:

```
                        Name: IL-1 eta

1 GGCACGAGGT TCCTCCCCAC TCTGTCTTTC TCACCTCTCC TTCACTTTTC  (SEQ ID NO:1)

51 CTAGCCTCCT CACCACCATC TGATCTATCT TGTTCTCTTC ACAAAAGGCT

101 CTGAAGACAT CATGAACCCA CAACGGGAGG CAGCACCCAA ATCCTATGCT

151 ATTCGTGATT CTCGACAGAT GGTGTGGGTC CTGAGTGGAA ATTCTTTAAT

201 AGCAGCTCCT CTTAGCCGCA GCATTAAGCC TGTCACTCTT CATTTAATAG

251 CCTGTAGAGA CACAGAATTC AGTGACAAGG AAAAGGGTAA TATGGTTTAC

301 CTGGGAATCA AGGGAAAAGA TCTCTGTCTC TTCTGTGCAG AAATTCAGGG

351 CAAGCCTACT TTGCAGCTTA AGGAAAAAAA TATCATGGAC CTGTATGTGG

401 AGAAGAAAGC ACAGAAGCCC TTTCTCTTTT TCCACAATAA AGAAGGCTCC

451 ACTTCTGTCT TTCAGTCAGT CTCTTACCCT GGCTGGTTCA TAGCCACCTC

501 CACCACATCA GGACAGCCCA TCTTTCTCAC CAAGGAGAGA GGCATAACTA

551 ATAACACTAA CTTCTACTTA GATTCTGTGG AATAA
```

The amino acid sequence of the polypeptides encoded by the nucleotide sequence of the invention include:

| Name: IL-1 eta (polypeptide) |
|---|
| 1 MNPQREAAPK SYAIRDSRQM VWVLSGNSLI AAPLSRSIKP VTLHLIACRD (SEQ ID NO:2) |
| 51 TEFSDKEKGN MVYLGIKGKD LCLFCAEIQG KPTLQLKEKN IMDLYVEKKA |
| 101 QKPFLFFHNK EGSTSVFQSV SYPGWFIATS TTSGQPIFLT KERGITNNTN |
| 151 FYLDSVE* |

The discovery of the IL-1 eta polynucleotides of the invention enables the construction of expression vectors comprising polynucleotide sequences encoding the respective polypeptides and host cells transfected or transformed with the expression vectors. The invention also enables the isolation and purification of biologically active IL-1 eta polypeptides and fragments thereof. In yet another embodiment, the polynucleotides or oligonucleotides thereof can be used as probes to identify DNA encoding proteins having activities associated with IL-1 family members. In addition, the polynucleotides or oligonucleotides thereof of the present invention may be used to identify human chromosome 2. Similarly, the polynucleotides or oligonucleotides thereof of the present invention may be used to map genes on human chromosome 2, and to identify genes associated with certain diseases, syndromes or other human conditions associated with human chromosome 2. Among such diseases, syndromes or conditions are glaucoma, ectodermal dysplasia, insulin-dependent diabetes mellitus, wrinkly skin syndrome, T-cell leukemia/lymphoma, and tibial muscular dystrophy. Finally, single-stranded sense or antisense oligonucleotides from these polynucleotides can be used to inhibit expression of polynucleotides encoded by the IL-1 eta.

Further, and in accordance with the present invention, IL-1 eta polypeptides and/or soluble fragments thereof, can be used to activate and/or inhibit the activation of vascular endothelial cells and lymphocytes, induce and/or inhibit the induction of local tissue destruction and fever (Janeway et al., 1996), inhibit and/or stimulate macrophages and vascular endothelial cells to produce IL-6, induce and/or inhibit the induction of prostaglandins, nitric oxide synthetase, and metalloproteinases, and upregulate and/or inhibit the upregulation of molecules on the surface of vascular endothelial cells. In addition these polypeptides and fragmented peptides can also be used to induce and/or inhibit the induction of inflammatory mediators such as transcription factors NF-κB and AP-1, MAP kinases JNK and p38, COX-2, iNOS, and all of the activities stimulated by these molecules. The polypeptides of this invention, and fragments thereof, can be used to generate antibodies, and the invention includes the use of such antibodies to purify IL-1 eta polypeptides.

Polynucleotide Molecules

In one embodiment, the present invention involves certain polynucleotides that are free from contaminating endogenous material. A polynucleotide refers to a DNA molecule in the form of a separate fragment or as a component of a larger polynucleotide construct. The polynucleotide molecule has been derived from DNA or RNA isolated at least once in a quantity that allows identification of its component nucleotide sequence by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region. In one embodiment of the instant invention, the open reading frame runs from nucleotide 112 to the TAA stop codon.

Polynucleotide molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, or a suitable fragment thereof, as a probe.

The DNA molecules of the invention include full length genes as well as polynucleotides and fragments thereof. The full length gene may include the N-terminal signal peptide. Other embodiments include DNA encoding a soluble form, e.g., encoding the extracellular domain of the protein, either with or without the signal peptide.

The polynucleotides of the invention are preferentially derived from human sources, but the invention includes those derived from non-human species, as well.

The particularly preferred polynucleotide of the invention has the polynucleotide sequence shown in the encoding region of SEQ ID NO:1 (beginning at nucleotide 112), for IL-1 eta. cDNA clones having the nucleotide sequence of SEQ ID NO:1 were isolated as described in Example 1. The polypeptide encoded by the IL-1 eta DNA of SEQ ID NO:1 is shown in SEQ ID NO:2.

The polypeptide of SEQ ID NO:2 shares homology with other IL-1 family members.

Due to the known degeneracy of the genetic code, wherein more than one codon can encode the same amino acid, a DNA can vary from that shown in SEQ ID NO:1, and still encode a polypeptide having the amino acid sequence of SEQ ID NO:2. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide resides 112–585 of SEQ ID NO:1; (b) DNA encoding the polypeptides of SEQ ID NO:2; (c) DNA that is the complement of DNA that is capable of hybridization to a DNA of (a) or (b) under conditions of moderate stringency and which encodes polypeptides of the invention; (d) DNA that is the complement of DNA capable of hybridization to a DNA of (a) or (b) under conditions of high stringency and which encodes polypeptides of the invention, and (e) DNA which is degenerate, as a result of the genetic code, to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual*, 2 ed. Vol. 1, pp. 1.101–104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the polynucleotide molecules of the invention also comprise nucleotide sequences that are at least 80% identical to a native sequence. Also contemplated are embodiments in which a polynucleotide molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two polynucleotide sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention provides isolated polynucleotides useful in the production of polypeptides. Such polypeptides may be prepared by any of a number of conventional techniques. A DNA sequence encoding a polypeptide of the invention, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189–196; and *PCR Protocols: A Guide to Methods and Applications*, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

The polypeptides of the invention include full length proteins encoded by the polynucleotide sequences set forth above. Particularly preferred polypeptides of IL-1 eta comprise the amino acid sequence of SEQ ID NO:2.

The polypeptides of the invention may be secreted and, thus, soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain a desired biological activity. Particular embodiments are directed to polypeptide fragments of SEQ ID NO:2 that retain the ability to bind the native cognates, substrates, or counter-structure ("binding partner"). Such a fragment may be a soluble polypeptide, as described above. In another embodiment, the polypeptides and fragments advantageously include regions that are conserved in the IL-1 ligand and IL-1 receptor family as described above.

Also provided herein are polypeptide fragments comprising at least 20, or at least 30, contiguous amino acids of the sequences of SEQ ID NO:2. Polypeptide fragments also may be employed as immunogens, in generating antibodies.

Naturally occurring variants as well as derived variants of the polypeptides and fragments are provided herein. Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1–5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain IL-1 eta polypeptides. Such oligomers may be in the form of covalently linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-Based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1–10.19.11, 1992).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151, hereby incorporated by reference, is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992–4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four polypeptide extracellular region.

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble polypeptides of the invention, separated by peptide linkers.

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240: 1759, 1988). The products of the nuclear oncogenes fos and jun comprise zipper domains that preferentially form heterodimers (O'Shea et al., *Science* 245:646, 1989, Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been reported recently to play a role in oligomerization of heat-shock transcription factors (Rabindran et al., *Science* 259:230, 1993).

Zipper domains fold as short, parallel coiled coils. (O'Shea et al., *Science* 254:539; 1991) The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated $(abcdefg)_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al. (*Science* 262:1401, 26 Nov. 1993)

Examples of leucine zipper domains suitable for producing soluble oligomeric proteins are described in PCT application WO 94/10308, and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267–278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD), as described in Hoppe et al. (*FEBS Letters* 344:191, 1994) and in U.S. Pat. No. 5,716, 805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr (SEQ ID NO:4).

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg, as described in U.S. Pat. No. 5,716,805 (SEQ ID NO:5). In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric oligomers. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the polynucleotide sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture,* 1990, pp. 15–69). Additional protocols using commercially available reagents, such as Lipofectamine lipid reagent (Gibco/BRL) or Lipofectamine-Plus lipid reagent, can be used to transfect cells (Feigner et al., *Proc. Natl. Acad. Sci. USA* 84:7413–7417, 1987). In addition, electroporation can be used to transfect mammalian cells using conventional procedures, such as those in Sambrook et al. (*Molecular Cloning: A Laboratory Manual,* 2 ed. Vol. 1–3, Cold Spring Harbor Laboratory Press, 1989). Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology,* 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology,* 1997, pp. 529–534 and PCT Application WO 97/25420) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Polynucleotides Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology,* 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology,* 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Another useful expression vector, pFLAG®, can be used. FLAG® technology is centered on the fusion of a low molecular weight (1 kD), hydrophilic, FLAG® marker peptide to the N-terminus of a recombinant protein expressed by pFLAG® expression vectors.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reverse-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means. For example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first are incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Screening Assays

The purified polypeptides of the invention (including proteins, polypeptides, fragments, variants, oligomers, and other forms) may be tested for the ability to bind the binding partner in any suitable assay, such as a conventional binding assay. The polypeptide may be labeled with a detectable reagent (e.g., a radionuclide, chromophore, enzyme that catalyzes a colorimetric or fluorometric reaction, and the like). The labeled polypeptide is contacted with cells expressing the binding partner. The cells then are washed to remove unbound labeled polypeptide, and the presence of cell-bound label is determined by a suitable technique, chosen according to the nature of the label.

Another type of suitable binding assay is a competitive binding assay. Competitive binding assays can be performed by conventional methodology. Reagents that may be employed in competitive binding assays include radiolabeled polypeptides of the invention and intact cells expressing the binding partner (endogenous or recombinant). For example, a radiolabeled soluble IL-1 eta fragment can be used to compete with a soluble IL-1 eta variant for binding to cell surface IL-1 eta receptors. Instead of intact cells, one could substitute a soluble binding partner/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled soluble binding partner, such as a soluble IL-1 eta receptor/Fc fusion protein, and intact cells expressing the binding partner. Qualitative results can be obtained by competitive autoradiographic plate binding assays, while Scatchard plots (Scatchard, *Ann. N.Y. Acad. Sci.* 51:660, 1949) may be utilized to generate quantitative results. Such binding assays may be useful in evaluating the biological activity of a variant polypeptide by assaying for the variant's ability to compete with the native protein for binding to the binding partner.

The IL-1 eta polypeptide of the present invention may also be used in a screening assay for compounds and small molecules which inhibit activation by (antagonize) the IL-1 eta polypeptide of the instant invention. Thus, polypeptides of the invention may be used to identify antagonists from, for example, cells, cell-free preparations, chemical libraries, and natural product mixtures. The antagonists may be natural or modified substrates, ligands, enzymes, receptors, etc. of the IL-1 eta polypeptide, or may be structural or functional mimetics of the IL-1 eta polypeptide. The antagonists may further be small molecules, peptides, antibodies and antisense oligonucleotides.

One embodiment of a method for identifying compounds which antagonize the IL-1 eta polypeptide is contacting a candidate compound with cells which respond to IL-1 eta polypeptide and observe the binding of IL-1 eta to the cells, or stimulation or inhibition of a functional response. The activity of the cells which were contacted with the candidate compound could then be compared with the identical cells which were not contacted for IL-1 eta polypeptide activity and IL-1 eta polypeptide agonists and antagonists could be identified. A still further embodiment of the instant invention provides a method of identifying compounds that inhibit the synthesis or secretion of IL-1 eta by contacting the candidate compound with cells which express IL-1 eta polypeptide and measuring the IL-1 eta production. The measurement of IL-1 eta production could be performed by a number of well-known methods such as measuring the amount of protein present (e.g. an ELISA) or of the protein's activity.

Drug Discovery

The purified polypeptides according to the invention will facilitate the discovery of inhibitors (or antagonists) and/or agonists of such polypeptides. The use of a purified polypeptide of the invention in the screening of potential inhibitors and/or agonists thereof is important and can eliminate or reduce the possibility of interfering reactions with contaminants.

In addition, polypeptides of the invention can be used for structure-based design of polypeptide-inhibitors and/or agonists. Such structure-based design is also known as "rational drug design." The polypeptides can be three-dimensionally analyzed by, for example, X-ray crystallography, nuclear magnetic resonance or homology modeling, all of which are well-known methods. The use of the polypeptide structural information in molecular modeling software systems to assist in inhibitor design and inhibitor-polypeptide interaction is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of polypeptides of the invention for likely binding sites of substrates, synthesizing a new molecule that incorporates a predictive reactive site, and assaying the new molecule as described above.

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays. Homogeneous assays are preferred. Also comprehended herein are cell-based assays, for example those utilizing reporter genes, as well as functional assays that analyze the effect of an antagonist or agonist on biological function(s) or activity(ies) of IL-1 eta (for example, stimulation of the secretion of cytokines or inhibition thereof, as disclosed herein). Moreover, animal models of inflammatory conditions are useful assays of biological activity.

Accordingly, in one aspect of the invention, there is provided a method for screening a test compound to determine whether the test compound affects (or modulates) a biological activity of an IL-1 eta polypeptide, the method comprising contacting the test compound and the IL-1 eta polypeptide with cells capable of exhibiting the biological activity when contacted with IL-1 eta, and analyzing the cells for the occurrence of the biological activity, wherein if the biological activity observed in the presence of the test compound differs from the biological activity that is observed when the test compound is absent, the test compound affects the biological activity of the IL-1 eta. The cells may be contacted in vitro or in vivo.

As used herein, the IL-1 eta polypeptide comprises a polypeptide selected from the group consisting of the polypeptides of SEQ ID NO:2, and polypeptides encoded by DNAs that hybridize under moderately stringent conditions to the DNA of SEQ ID NO:1. Such polypeptides include polypeptides comprising variant amino acid sequences that are at least 80% identical to the polypeptides of SEQ ID NO:2 (preferably, the variant amino acid sequences that are at least 90% identical, more preferably at least 95% identical, most preferably at least 97% identical, to the polypeptides of SEQ ID NO:2). Additional examples of useful IL-1 eta polypeptides include polypeptides comprising the amino acid sequences of SEQ ID NO:2 wherein the polypeptides comprise alterations to the amino acid sequences selected from the group consisting of inactivated N-glycosylation site(s), inactivated protease processing site(s), conservative amino acid substitution(s), and combinations thereof. Moreover, fragments of the aforesaid polypeptides that have at least one activity of IL-1 eta as described below are also comprehended herein.

IL-1 eta biological activity includes, but is not limited to, modulation of cytokine expression, modulation of the expression of molecules indicative of activation of an immune or inflammatory response (for example, COX2, iNOS), modulation of cell-surface molecule expression, modulation of activation of one or more signaling cascades, modulation of induction of mRNAs for the aforementioned proteins, modulation of induction of cell proliferation and/or cell death, induction of morphological and/or functional changes in cells, and combinations thereof. The inventive methods comprise methods of assaying for any of these biological activities. Those of skill in the art will recognize that modulation of cytokines means that the levels of expression of certain cytokines increase while the levels of other cytokines decreases, and that such combinations are comprehended in the term modulation; the same is true for other activities of IL-1 eta.

When the methods of the present invention include assaying for IL-1 eta modulation of cytokine expression, cytokines that may be assayed include (but are not limited to) IL-1 alpha, IL-1 beta, TNF-alpha, IL-10, IFN-gamma, IL-12 (in particular, the p40 subunit), IL-6, IL-1ra, IL-4, IL-13, GM-CSF, IL-18, IL-1 homologs such as IL-1 epsilon, IL-1 eta, IL-1 theta, IL-1 zeta, and IL-1 H1, and combinations thereof. Similarly, when the screening methods of the present invention include assaying for IL-1 eta modulation of cell surface molecule expression, the cell surface molecules that may be assayed include ICAM-1, TLR4, TLR5, TLR9, DC-B7, MHC class I and II antigens, VCAM, ELAM, B7-1, B7-2, CD40L, and combinations thereof.

IL-1 eta mediated modulation of signaling pathways often involves a cascade of molecular changes, for example as discussed previously wherein a receptor propagates a ligand-receptor mediated signal by specifically activating intracellular kinases which phosphorylate target substrates (which can themselves be kinases that become activated following phosphorylation, or adaptor molecules that facilitate downstream signaling through protein-protein interaction following phosphorylation), resulting in the activation of other factors (for example, NFkappaB). When the screening methods of the present invention include assaying for IL-1 eta induced modulation of signaling pathways, the signaling pathways that may be assayed include those involving activation of NFkappaB. Assaying for activation signaling cascades further includes detecting phosphorylation of molecules that occurs during the signaling cascade, as in the phosphorylation of IkappaB (including IkappaB degradation assays, and assays for free IkappaB), p38 MAP kinase, and Stress-Activated Protein Kinase (SAPK/JNK).

Moreover, those of skill in the art understand that biological activity(ies) is/are most often induced by the binding of a ligand (i.e., IL-1 eta) to a receptor (counterstructure or binding moiety) present on a cell; accordingly, as previously described, IL-1 eta polypeptides (including IL-1 eta polypeptide fragments) can be used in binding studies to identify receptor-expressing cells. Such binding studies also provide assays useful in the inventive methods. IL-1 eta polypeptides may also be used to clone receptors (or other molecules that bind IL-1 eta) and to screen for molecules that block receptor/ligand interactions. Those of ordinary skill in the art further understand that biological activities include cell proliferation, cell death, and changes in cell morphology and/or function (for example, activation, maturation); assays that evaluate such effects of IL-1 eta are known in the art, and will also be useful in the inventive methods. Moreover, animal models of syndromes and/or conditions, such as those disclosed herein, are useful for screening compounds for biological activity, including screening for antagonism (or agonism) of IL-1 eta.

The inventive methods further encompass performing more than one assay to discover and/or analyze agonists or antagonists of IL-1 eta activity (i.e., combination methods). Generally, such methods comprise selecting test compounds that affect a property of IL-1 eta (i.e., an ability of IL-1 eta to bind an IL-1 eta counter structure), then testing the selected compounds for an effect on another property of IL-1 eta (i.e., contacting the selected test compounds and an IL-1 eta polypeptide with cells capable of exhibiting a biological activity when contacted with IL-1 eta, and determining whether the compounds affect the biological activity). For example, the inventive methods may comprise a first assay to determine whether a candidate molecule interacts with (binds to) IL-1 eta. In one embodiment, the first assay is in a high throughput format, numerous forms of which are known in the art and disclosed herein. Such an assay will generally comprise the steps of: contacting test compounds and an IL-1 eta polypeptide with an IL-1 eta counterstructure; determining whether the test compounds affect the ability of IL-1 eta to bind the counterstructure; and selecting one or more test compounds that affect the ability of IL-1 eta to bind the counterstructure. The inventive combination methods further comprise evaluating selected compounds in a second assay, for agonistic or antagonistic effect on biological activity using one or more of the aforementioned assays.

Alternatively, the inventive combination methods may comprise a first assay to determine whether a candidate molecule modulates a biological activity of IL-1 eta, as described herein using an in vitro assay or an in vivo assay (for example, an animal model). According to such combination methods, molecules that modulate an IL-1 eta biological activity in this manner are selected using one or more of the aforementioned assays for biological activity, and assayed to determine whether the candidate molecule(s) bind IL-1 eta. The selected molecules may be tested to further define the exact region or regions of IL-1 eta to which the test molecule binds (for example, epitope mapping for antibodies).

As disclosed previously, the types of assays for biological activities of IL-1 eta that can be used in the inventive combination methods include assays for the expression of cytokines, assays for the expression of cell-surface molecules, assays to detect activation of signaling molecules, assays to detect induction of mRNAs, and assays that evaluate cell proliferation or cell death (and combinations thereof), as described herein. Molecules that bind and that have an agonistic or antagonistic effect on biologic activity will be useful in treating or preventing diseases or conditions with which the polypeptide(s) are implicated.

Those of ordinary skill in the art understand that when the biological activity observed in the presence of the test compound is greater than that observed when the test compound is absent, the test compound is an agonist of IL-1 eta, whereas when the biological activity observed in the presence of the test compound is less than that observed when the test compound is absent, the test compound is an antagonist (or inhibitor) of IL-1 eta. Generally, an antagonist will decrease or inhibit, an activity by at least 30%; more preferably, antagonists will inhibit activity by at least 50%, most preferably by at least 90%. Similarly, an agonist will increase, or enhance, an activity by at least 20%; more preferably, agonists will enhance activity by at least 30%, most preferably by at least 50%. Those of skill in the art will also recognize that agonists and/or antagonists with different levels of agonism or antagonism respectively may be useful for different applications (i.e., for treatment of different disease states).

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions (including protein-protein, receptor-ligand, enzyme-substrate, and so on), and the inhibition thereof by small organic molecules. These assay methods and techniques are well known in the art (see, e.g., High Throughput Screening: The Discovery of Bioactive Substances, John P. Devlin (ed.), Marcel Dekker, New York, 1997 ISBN: 0-8247-0067-8). The screening assays of the present invention are amenable to high throughput screening of chemical libraries and are suitable for the identification of small molecule drug candidates, antibodies, peptides, and other antagonists and/or agonists, natural or synthetic. Several useful assays are disclosed in U.S. Ser. No. 09/851,673, filed May 8, 2001 (the relevant disclosure of which is hereby incorporated by reference).

Candidate Molecules to be Tested:

The methods of the invention may be used to identify antagonists (also referred to as inhibitors) and agonists of IL-1 eta activity from cells, cell-free preparations, chemical libraries, cDNA libraries, recombinant antibody libraries (or libraries comprising subunits of antibodies) and natural product mixtures. The antagonists and agonists may be natural or modified substrates, ligands, enzymes, receptors, etc. of the polypeptides of the instant invention, or may be structural or functional mimetics of IL-1 eta or its binding partner/counterstructure. Potential antagonists of the instant invention include small molecules, peptides and antibodies that bind to and occupy a binding site of the inventive polypeptides or a binding partner thereof, causing them to be unavailable to bind to their natural binding partners and therefore preventing normal biological activity. Antagonists also include chemicals (including small molecules and peptides) that interfere with the signaling pathways used by IL-1 eta (for example, by inhibiting the interaction of receptor subunits, or inhibiting the interaction of intracellular components of the signaling cascade). Potential agonists include small molecules, peptides and antibodies which bind to the instant polypeptides or binding partners thereof, and elicit the same or enhanced biologic effects as those caused by the binding of the polypeptides of the instant invention. Moreover, substances that activate (or enhance) the signaling pathways used by IL-1 eta are also included within the scope of agonists of IL-1 eta.

Small molecule agonists and antagonists are usually less than 10K molecular weight and may possess a number of physicochemical and pharmacological properties which enhance cell penetration, resist degradation and prolong their physiological half-lives (Gibbs, J., Pharmaceutical Research in Molecular Oncology, Cell, Vol. 79 (1994)). Antibodies, which include intact molecules as well as fragments such as Fab and F(ab')2 fragments, as well as recombinant molecules derived therefrom (including antibodies expressed on phage, intrabodies, single chain antibodies such as scFv and other molecules derived from immunoglobulins that are known in the art), may be used to bind to and inhibit the polypeptides of the instant invention by blocking the propagation of a signaling cascade. It is preferable that the antibodies are humanized, and more preferable that the antibodies are human. The antibodies of the present invention may be prepared by any of a variety of well-known methods, as disclosed herein.

Additional examples of candidate molecules, also referred to herein as "test molecules" or "test compounds," to be tested for the ability to modulate IL-1 eta activity include, but are not limited to, carbohydrates, small molecules (usually organic molecules or peptides), proteins, and nucleic acid molecules (including oligonucleotide fragments typically consisting of from 8 to 30 nucleic acid residues). Peptides to be tested typically consist of from 5 to 25 amino acid residues. Also, candidate nucleic acid molecules can be antisense nucleic acid sequences, and/or can possess ribozyme activity.

Small molecules to be screened using the hereindescribed screening assays can typically be administered orally or by injection to a patient in need thereof. Small molecules that can be administered orally are especially preferred. The small molecules of the invention preferably will not be toxic (or only minimally toxic) at the doses required for them to be effective as pharmaceutical agents, and they are preferably not subject to rapid loss of activity in the body, such as the loss of activity that might result from rapid enzymatic or chemical degradation. In addition, pharmaceutically useful small molecules are preferably not immunogenic.

The methods of the invention can be used to screen for antisense molecules that inhibit the functional expression of one or more mRNA molecules that encode one or more proteins that mediate an IL-1 eta-dependent cellular response. An anti-sense nucleic acid molecule is a DNA sequence that is capable of can hybridizing to the target mRNA molecule through Watson-Crick base pairing, and inhibiting translation thereof. Alternatively, the DNA may be inverted relative to its normal orientation for transcription and so express an RNA transcript that is complementary to the target mRNA molecule (i.e., the RNA transcript of the anti-sense nucleic acid molecule can hybridize to the target mRNA molecule through Watson-Crick base pairing). An anti-sense nucleic acid molecule may be constructed in a number of different ways provided that it is capable of interfering with the expression of a target protein. Typical anti-sense oligonucleotides to be screened preferably are 30–40 nucleotides in length. The anti-sense nucleic acid molecule generally will be substantially identical (although in antisense orientation) to the target gene. The minimal identity will typically be greater than about 80%, but a higher identity might exert a more effective repression of expression of the endogenous sequences. Substantially greater identity of more than about 90% is preferred, though about 95% to absolute identity would be most preferred.

Candidate nucleic acid molecules can possess ribozyme activity. Thus, the methods of the invention can be used to screen for ribozyme molecules that inhibit the functional expression of one or more mRNA molecules that encode one or more proteins that mediate an IL-1 eta dependent cellular response. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

The design and use of target RNA-specific ribozymes is described in Haseloff et al. (Nature, 334:585, 1988; see also U.S. Pat. No. 5,646,023), both of which publications are incorporated herein by reference. Tabler et al. (Gene 108: 175, 1991) have greatly simplified the construction of catalytic RNAs by combining the advantages of the anti-sense RNA and the ribozyme technologies in a single construct. Smaller regions of homology are required for ribozyme catalysis, therefore this can promote the repression of different members of a large gene family if the cleavage sites are conserved.

Use of IL-1 eta Polynucleotides and Oligonucleotides

Among the uses of polynucleotides of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO:1, from other mammalian species, are contemplated herein, probes based on the human DNA sequence of SEQ ID NO:1 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Polynucleotides encoding SEQ ID NO:2 or oligonucleotide fragments of such polynucleotides, can be used by those skilled in the art using well-known techniques to identify the human chromosome 2, as well as the specific locus thereof, that contains the DNA of IL-1 ligand family members. Useful techniques include, but are not limited to, using polynucleotides or fragments as probes or primers in techniques that include radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization which can include performing PCR amplification using the Whitehead Institute/MIT Center for Genome Research Genebridge4 panel of 93 radiation hybrids (on the world-wide web (www-) at genome.wi.m-it.edu/ftp/-distribution/human_STS_releases/july97/rhmap/genebridge4.html). Useful PCR primers are those that lie within the gene of interest and which amplify a product from human genomic DNA, but do not amplify hamster genomic DNA. The products of the PCR reactions are converted into a data vector that is submitted to the Whitehead/MIT Radiation Mapping site on the Internet (on the world-wide web (www-) at seq.wi.mit.edu). The data is scored and the chromosomal assignment and placement relative to known Sequence Tag Site (STS) markers on the radiation hybrid map is provided. The web site on the world-wide web (www-) at genome.wi.mit.edulftp/distribution/-human_STS$_{13}$reieases/j u1y97/07-97.INTRO.html) also provides information about radiation hybrid mapping.

As set forth below, using radiation hybridization, the polynucleotide of SEQ ID NO:1 is shown to map to the 2q11-12 region of human chromosome 2. Human chromosome 2 is associated with specific diseases which include but are not limited to glaucoma, ectodermal dysplasia, insulin-dependent diabetes mellitus, wrinkly skin syndrome, T-cell leukemia/lymphoma, and tibial muscular dystrophy. Thus, the polynucleotide of SEQ ID NO:1 or a fragment thereof can be used by one skilled in the art using well-known techniques to analyze abnormalities associated with gene mapping to chromosome 2. This enables one to distinguish conditions in which this marker is rearranged or deleted. In addition, the polynucleotide of SEQ ID NO:1 or a fragment thereof can be used as a positional marker to map other genes of unknown location.

DNA of the present invention may be used in developing treatments for any disorder mediated (directly or indirectly) by defective, or insufficient amounts of, the genes corresponding to the polynucleotides of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Other useful fragments of the polynucleotides of this invention include antisense or sense oligonucleotides comprising a single-stranded polynucleotide sequence (either RNA or DNA) capable of binding to target mRNA (sense) or DNA (antisense) sequences. Antisense or sense oligonucleotides according to the present invention comprise a fragment of DNA (SEQ ID NO:1). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding antisense or sense oligonucleotides to target polynucleotide sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target polynucleotide sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target polynucleotide sequence by any gene transfer method, including, for example, lipofection, CaPO$_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target polynucleotide sequence by formation of an oligonucleotide-lipid complex, as described in WO 90/10448. The sense or antisense oligonucleotide-lipid complex is preferably dissociated within the cell by an endogenous lipase.

Uses of IL-1 eta Polypeptides and Fragmented Polypeptides

Polypeptides of the present invention find use as a protein purification reagent. The polypeptides may be attached to a solid support material and used to purify the binding partner proteins by affinity chromatography. In particular embodiments, a polypeptide (in any form described herein that is capable of binding the binding partner) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express the binding partner on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing the binding partner expressing cells are contacted with the solid phase having the polypeptides thereon. Cells expressing the binding partner on the cell surface bind to the fixed polypeptides, and unbound cells then are washed away.

Alternatively, the polypeptides can be conjugated to a detectable moiety, then incubated with cells to be tested for binding partner expression. After incubation, unbound labeled matter is removed and the presence or absence of the detectable moiety on the cells is determined.

In a further alternative, mixtures of cells suspected of containing cells expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods.

Polypeptides also find use in measuring the biological activity of the binding partner protein in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a binding partner protein that has been stored at different temperatures, or produced in different cell types. The proteins also may be used to determine whether biological activity is retained after modification of a binding partner protein (e.g., chemical modification, truncation, mutation, etc.). The binding affinity of the modified binding partner protein is compared to that of an unmodified binding partner protein to detect any adverse impact of the modifications on biological activity of the binding partner. The biological activity of a binding partner protein thus can be ascertained before it is used in a research study, for example.

The polypeptides also find use as carriers for delivering agents attached thereto to cells bearing the binding partner. The polypeptides thus can be used to deliver diagnostic or therapeutic agents to such cells (or to other cell types found to express the binding partner on the cell surface) in in vitro or in vivo procedures.

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Polypeptides of the invention may be used in developing treatments for any disorder mediated (directly or indirectly) by defective, or insufficient amounts of the polypeptides. Further, the polypeptides of the invention may be used in developing treatments for any disorder resulting (directly or indirectly) from an excess of the polypeptide. The polypeptides of the instant invention may be administered to a mammal afflicted with such disorders.

The polypeptides may also be employed in inhibiting a biological activity of the binding partner, in in vitro or in vivo procedures. For example, a purified IL-1 eta polypeptide can be used to inhibit binding of endogenous IL-1 eta to its cell surface receptor.

Polypeptides of the invention may be administered to a mammal to treat a binding partner-mediated disorder. Such binding partner-mediated disorders include conditions caused (directly or indirectly) or exacerbated by the binding partner.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble polypeptides of the invention.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Those of ordinary skill in the art recognize that other types of localized administration (e.g., intraarticular, intracapsular, intracarpal, intracelial, intracerebroventricular, intrasynovial, intraspinal, intraligamentus, intrameningeal, intraocular, epidural, transepithelially, and/or administration by one or more of these routes at a site near or adjacent to a site of disease or injury) are suitable for use in administering the compositions of the present invention. Sustained release from implants is also contemplated.

One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising polynucleotides in physiologically acceptable formulations are also contemplated. DNA may be formulated for injection, for example. Moreover, inasmuch as those of ordinary skill in the art are aware that nucleic acid compositions (including DNA) are taken up by cells and result in the expression of protein in or near the area where the nucleic acid composition was administered, the inventive nucleic acid compositions will be useful for localized administration of polypeptides encoded thereby.

Another use of the polypeptide of the present invention is as a research tool for studying the biological effects that result from the interactions of IL-1 eta with its binding partner, or from inhibiting these interactions, on different cell types. Polypeptides also may be employed in it vitro assays for detecting IL-1 eta, the binding partner or the interaction thereof. The inventive polypeptides will also be useful in elucidating the signaling pathways of IL-1 family members, and in identifying molecules that modulate various aspects of such signaling pathways. The modulators identified by studies utilizing the inventive polypeptides have utility in treating or ameliorating a wide variety of diseases and syndromes in which the inflammatory response plays a role.

Another embodiment of the invention relates to uses of the polypeptides of the invention to study cell signal transduction. IL-1 family ligands play a central role in protection against infection and immune inflammatory responses which includes cellular signal transduction, activating vascular endothelial cells and lymphocytes, induction of inflammatory cytokines, acute phase proteins, hematopoiesis, fever, bone resorption, prostaglandins, metalloproteinases, and adhesion molecules. With the continued increase in the number of known IL-1 family members, a suitable classification scheme is one based on comparing polypeptide structure as well as function (activation and regulatory properties). Thus, IL-1 eta, like other IL-1 family ligands (IL-1α, IL-1β, and IL-18) are likely involved in many of the functions noted above as well as promote inflammatory responses and therefore be involved in the causation and maintenance of inflammatory and/or autoimmune diseases such as rheumatoid arthritis, inflammatory bowel disease, and psoriasis. As such, alterations in the expression and/or activation of the polypeptides of the invention can have profound effects on a plethora of cellular processes, including, but not limited to, activation or inhibition of cell specific responses and proliferation. Expression of cloned IL-1 eta, or of functionally inactive mutants thereof, can be used to identify the role a particular protein plays in mediating specific signaling events.

Accordingly, IL-1 eta has therapeutic uses, such as protecting against infection and generating immune and inflammatory responses in individuals whose immune and inflammatory responses are inappropriate or nonresponsive. For example, IL-1 eta may be useful in stimulating the immune system of individuals whose immune system is immunosuppressed. Similarly, because IL-1 eta likely promotes inflammatory responses and is involved in the causation and maintenance of inflammatory and/or autoimmune diseases, antagonists of IL-1 eta are useful in inhibiting or treating inflammatory and/or automimmune disease. Thus, antagonists of IL-1 eta will be useful in treating inflammatory bowel disease (for example, Crohn's disease and ulcerative colitis), multiple sclerosis (MS) and other demyelinating conditions, and asthma or other pulmonary conditions in which an immune or inflammatory response is involved (for example, infection-associated airway hyperactivity, granulomatous lung disease, emphysema and chronic fibrosing alveolitis and acute hyperoxic lung damage).

IL-1 mediated cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed functionally active versions of IL-1 eta and its binding partners can be used to identify what substrate(s) were recognized and activated by the polypeptides of the invention. As such, these novel polypeptides can be used as reagents to identify novel molecules involved in signal transduction pathways.

Moreover, as described herein, IL-1 eta can be used to identify antagonists of such signaling pathways. Therefore, administration of IL-1 eta antagonists will have therapeutic application in blocking inflammatory responses, including the activation of transcription factors NFkappaB and API, the protein kinases Jun N-terminal kinase and p38 MAP kinase, the enzymes COX-2 leading to prostaglandin production and iNOS leading to nitric oxide production, and inflammation in general. Such signaling pathways have been shown to be involved in sepsis, septic, toxic or hemorhagic shock and acute respiratory distress, such as that which occurs in inhalational anthrax. Antagonists of IL-1 eta can be used in combination with other agents in the treatment of inflammatory dysregulation syndromes, including for example inhibitors of TNFalpha, inhibitors of other members of the IL-1 family, corticosteroids, and inhibitors of other mediators of inflammation such as macrophage migration inhibitory factor, and/or inhibitors of cell-surface receptors such as CD14 and Toll-like receptors.

Similarly, because IL-1 promotes inflammatory responses and is involved in the causation and maintenance of inflammatory and/or autoimmune diseases, antagonists of IL-1 eta are useful in inhibiting or treating inflammatory and/or autoimmune disease. Thus, IL-1 eta antagonists will be useful in treating arthritic conditions that have an inflammatory or autoimmune component, for example, rheumatoid arthritis and/or ankylosing spondylitis; inflammatory bowel disease, including Crohn's Disease and ulcerative colitis, and psoriasis (including psoriatic arthritis). Other inflammatory and/or autoimmune diseases in which IL-1 eta is implicated include pulmonary conditions relating to an immune or inflammatory response and/or in which airway hyperreactivity plays a role, for example, asthma, infection-associated airway hyperactivity, granulomatous lung disease, emphysema and chronic fibrosing alveolitis and acute hyperoxic lung damage, and demyelinating conditions that have an inflammatory or autoimmune component, for example, multiple sclerosis and/or chronic inflammatory demyelinating polyneuropathy. Accordingly, antagonists of IL-1 eta will also be useful in ameliorating these conditions.

Additional conditions for which an autoimmune and/or inflammatory component is a contributory factor (and thus, for which antagonists of IL-1 eta are useful) include cardiovascular conditions such as stroke, acute myocardial infarction, unstable angina, arterial restenosis and congestive heart failure. IL-1 eta antagonists are useful in treating or preventing osteoporosis and/or osteoarthritis, as well as glomerulonephritis, uveitis, and/or Behcet's syndrome. An autoimmune or inflammatory component also plays a role in the cause or maintenance of sepsis, acute pancreatitis, diabetes (particularly Type II, insulin dependent diabetes), endometriosis, and periodontal disease. Similarly, the inflammatory response causes or exacerbates heat stroke and glaucoma, and the cytokines involved in the immune/inflammatory response play a supportive role in neoplastic disease (for example, in multiple myeloma and/or myeloid leukemia), facilitating the growth of neoplastic cells. Accordingly, IL-1 eta antagonists are useful in treating or ameliorating these conditions by downregulating the immune and/or inflammatory response that plays a causative role therein.

Moreover, as disclosed in United States Patent Application 20010026801 A1, published Oct. 4, 2001, other syndromes and/or conditions are caused or exacerbated by localized production of proinflammatory cytokines. Accordingly, antagonists of IL-1 eta can be administered locally to ameliorate a localized inflammatory and/or autoimmune reaction. Such localized reactions occur, for example, in neurological disorders due to a herniated nucleus pulposus (herniated disk), osteoarthritis, other forms of arthritis, disorders of bone, disease, and/or trauma causing damage to the optic nerve, other cranial nerves, spinal cord, nerve roots, or peripheral nerves. Moreover, trauma, injury, compression and disease can affect individual nerves, nerve roots, the spinal cord, or localized areas of muscle. Disorders for which localized administration of antagonists of IL-1 are useful include spinal cord injury, spinal cord compression, spinal stenosis, carpal tunnel syndrome, glaucoma, Bell's palsy, localized muscular disorders (including acute muscle pulls, muscle sprains, muscle tears, and muscle spasm), Alzheimer's disease and post-herpetic neuralgia. Localized anti-inflammatory agents will also be useful for treatment of conditions in which fascia, tendons, ligaments or other structures of a joint, and/or other connective tissues are injured and/or inflamed (for example, tendonitis, bursitis, strained, sprained or torn ligaments, fascitis, etc.). Useful antagonists for localized administration in the aforementioned conditions includes localized administration of polypeptide compositions as well as nucleic acid compositions, as previously described herein.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to the binding partner may be used to inhibit a biological activity that results from such binding. Such blocking antibodies may be identified using any suitable assay procedure, such as by testing antibodies for the ability to inhibit binding of IL-1 eta to certain cells expressing the IL-1 eta receptors. Alternatively, blocking antibodies may be identified in assays for the ability to inhibit a biological effect that results from polypeptides of the invention binding to their binding partners to target cells. Antibodies may be assayed for the ability to inhibit IL-1 eta-mediated, or binding partner-mediated cell lysis, for example.

Such an antibody may be employed in an in vitro procedure, or administered in vivo to inhibit a biological activity mediated by the entity that generated the antibody. Disorders caused or exacerbated (directly or indirectly) by the interaction of the polypeptides of the invention with the binding partner thus may be treated. A therapeutic method involves in vivo administration of a blocking antibody to a mammal in an amount effective in inhibiting a binding partner-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to cell surface receptor, induce biological effects (e.g., transduction of biological signals) similar to the biological effects induced when IL-1 binds to cell surface IL-1 receptors. Agonistic antibodies may be used to activate vascular endothelial cells and lymphocytes, induce local tissue destruction and fever (Janeway et al., 1996), stimulate macrophages and vascular endothelial cells to produce IL-6, and upregulate molecules on the surface of vascular endothelial cells.

Compositions comprising an antibody that is directed against polypeptides of the invention, and a physiologically acceptable diluent, excipient, or carrier, are provided herein. Suitable components of such compositions are as described above for compositions containing polypeptides of the invention.

Also provided herein are conjugates comprising a detectable (e.g., diagnostic) or therapeutic agent, attached to the antibody. Examples of such agents are presented above. The conjugates find use in in vitro or in vivo procedures.

The following examples are offered by way of illustration, and not by way of limitation. Those skilled in the art will recognize that variations of the invention embodied in the examples can be made, especially in light of the teachings of the various references cited herein, the disclosures of which are incorporated by reference in their entirety.

EXAMPLE 1

Isolation of the IL-1 ETA Polynucleotides

Human genomic DNA containing the upstream portion of IL-1 eta cDNA as defined in EP O879889A2 was cloned and extended in the 3' direction. The genomic DNA was sequenced and examined for potential homology to the C-terminal section of IL-1 family members. A region with the potential to code with homology to the C-terminal section of IL-1 family members was located and is disclosed as polynucleotides 375 to 585 of SEQ. ID. NO.:1. PCR primers were synthesized containing the stop codon in the 3' or reverse primer, and the initiating ATG of the IL-1 eta cDNA (SEQ. ID. NO.:1 of EP 0879889A2) in the 5' or sense primer. Using these primers, IL-1 eta cDNA was amplified from first stand cDNA made from human tonsil mRNA. PCR was preformed using standard protocols.

EXAMPLE 2

Use of Purified IL-1 eta Polypeptides

Serial dilutions of IL-1 eta-containing samples (in 50 mM NaHCO$_3$, brought to pH 9 with NaOH) are coated onto Linbro/Fitertek 96 well flat bottom E.I.A. microtitration plates (ICN Biomedicals Inc., Aurora, Ohio) at 100:1/well. After incubation at 4° C. for 16 hours, the wells are washed six times with 200:1 PBS containing 0.05% Tween-20 (PBS-Tween). The wells are then incubated with FLAG®-binding partner at 1 mg/ml in PBS-Tween with 5% fetal calf serum (FCS) for 90 minutes (100:1 per well), followed by washing as above. Next, each well is incubated with the anti-FLAG® (monoclonal antibody M2 at 1 mg/ml in PBS-Tween containing 5% FCS for 90 minutes (100:1 per well), followed by washing as above. Subsequently, wells are incubated with a polyclonal goat anti-mIgG1-specific horseradish peroxidase-conjugated antibody (a 1:5000 dilution of the commercial stock in PBS-Tween containing 5% FCS) for 90 minutes (100:1 per well). The HRP-conjugated antibody is obtained from Southern Biotechnology Associates, Inc., Birmingham, Ala. Wells then are washed six times, as above.

For development of the ELISA, a substrate mix [100:1 per well of a 1:1 premix of the TMB Peroxidase Substrate and Peroxidase Solution B (Kirkegaard Perry Laboratories, Gaithersburg, Md.)] is added to the wells. After sufficient color reaction, the enzymatic reaction is terminated by addition of 2 N $H_2SO_4$ (50:1 per well). Color intensity (indicating ligand receptor binding) is determined by measuring extinction at 450 nm on a V Max plate reader (Molecular Devices, Sunnyvale, Calif.).

EXAMPLE 3

Amino Acid Sequence

The amino acid sequence of IL-1 eta was determined by translation of the nucleotide sequence of SEQ ID NO:1. The coding region includes nucleotide residues 112–585.

EXAMPLE 4

DNA and Amino Acid Sequences

The nucleotide sequence of the isolated IL-1 eta and the amino acid sequence encoded thereby, are presented in SEQ ID NOs:1 and 2. The sequence of the IL-1 eta DNA fragment isolated by PCR corresponds to nucleotides 1 to 585 of SEQ ID NO:1. Nucleotide residues 112–585 encode amino acids 1 to 157 of SEQ ID NO:2.

The amino acid sequence of SEQ ID NO:2 bears significant homology to other known IL-1 ligand family members.

EXAMPLE 5

Monoclonal Antibodies that Bind Polypeptides of the Invention

This example illustrates a method for preparing monoclonal antibodies that bind IL-1 eta. Suitable immunogens that may be employed in generating such antibodies include, but are not limited to, purified IL-1 eta polypeptide or an immunogenic fragment thereof such as the extracellular domain, or fusion proteins containing IL-1 eta (e.g., a soluble IL-1 eta/Fc fusion protein).

Purified IL-1 eta can be used to generate monoclonal antibodies immunoreactive therewith, using conventional techniques such as those described in U.S. Pat. No. 4,411, 993. Briefly, mice are immunized with IL-1 eta immunogen emulsified in complete Freund's adjuvant, and injected in amounts ranging from 10–100 g subcutaneously or intraperitoneally. Ten to twelve days later, the immunized animals are boosted with additional IL-1 eta emulsified in incomplete Freund's adjuvant. Mice are periodically boosted thereafter on a weekly to bi-weekly immunization schedule. Serum samples are periodically taken by retro-orbital bleeding or tail-tip excision to test for IL-1 eta antibodies by dot blot assay, ELISA (Enzyme-Linked Immunosorbent Assay) or inhibition of IL-1 eta receptor binding.

Following detection of an appropriate antibody titer, positive animals are provided one last intravenous injection of IL-1 eta in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified IL-1 eta by adaptations of the techniques disclosed in Engvall et al., (*Immunochem.* 8:871, 1971) and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c mice to produce ascites containing high concentrations of anti-IL-1 eta monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to IL-1 eta.

EXAMPLE 6

Northern Blot Analysis

The tissue distribution of IL-1 eta is investigated by Northern blot analysis, as follows. An aliquot of a radiolabeled riboprobe is added to two different human multiple tissue Northern blots (Clontech, Palo Alto, Calif.; Biochain, Palo Alto, Calif.). The blots are hybridized in 10× Denhardts, 50 mM Tris pH 7.5, 900 mM NaCl, 0.1% Na pyrophosphate, 1% SDS, 200 µg/mL salmon sperm DNA. Hybridization is conducted overnight at 63° C. in 50% formamide as previously described (March et al., *Nature* 315:641–647, 1985). The blots are then washed with 2×SSC, 0.1% SDS at 68° C. for 30 minutes. The cells and tissues with the highest levels of IL-1 eta mRNA are determined by comparison to control probing with a β-actin-specific probe.

Expression of IL-eta was also analyzed in several animal models of human disease by conventional real-time polymerase chain reaction (RT-PCR) substantially as described in U.S. Ser. No. 09/876,790, filed Jun. 6, 2001, and/or by TaqMan® RT-PCR (Applied Biosystems, Foster City, Calif.).). Total RNA from small or large intestine (colitis models: DSS-induced colitis, anti-CD-3 induced ileitis and MdrKO spontaneous colitis), spinal cord (multiple sclerosis [MS] models: EAE using SJL mice injected with PLP), or lung (asthma model: BALB/c/OVA-induced asthma model) was used to make first strand cDNA. The level of expression was subjectively scored as a function of relative ethidium bromide staining intensity.

Results of these experiments indicated that expression of IL-1 eta was upregulated in DSS-induced colitis. Accordingly, IL-1 eta is implicated in the cause or prolongation of inflammatory bowel disease, and antagonists thereof will be useful in treating or ameliorating inflammatory bowel disease in individuals afflicted with such conditions. Additionally, IL-1 eta appeared to be upregulated in the early stages of EAE, indicating that an antagonist thereof may be useful in treating or ameliorating MS and other demyelinating conditions. IL-1 eta was also upregulated in the OVA-induced asthma model, indicating that an antagonist thereof may be useful in treating or ameliorating asthma and other pulmonary conditions relating to an immune or inflammatory response.

EXAMPLE 7

Binding Assay

Full length IL-1 eta can be expressed and tested for the ability to bind IL-1 eta receptors. The binding assay can be conducted as follows.

A fusion protein comprising a leucine zipper peptide fused to the N-terminus of a soluble IL-1 eta polypeptide (LZ-IL-1 eta) is employed in the assay. An expression construct is prepared, essentially as described for preparation of the FLAG® (IL-1 eta) expression construct in Wiley et al. (*Immunity*, 3:673–682, 1995; hereby incorporated by reference), except that DNA encoding the FLAG® peptide was replaced with a sequence encoding a modified leucine zipper that allows for trimerization. The construct, in expression vector pDC409, encodes a leader sequence derived from human cytomegalovirus, followed by the leucine zipper moiety fused to the N-terminus of a soluble IL-1 eta polypeptide. The LZ-IL-1 eta is expressed in CHO cells, and purified from the culture supernatant.

The expression vector designated pDC409 is a mammalian expression vector derived from the pDC406 vector described in McMahan et al. (*EMBO J.* 10:2821–2832, 1991; hereby incorporated by reference). Features added to pDC409 (compared to pDC406) include additional unique restriction sites in the multiple cloning site (mcs); three stop codons (one in each reading frame) positioned downstream of the mcs; and a T7 polymerase promoter, downstream of the mcs, that facilitates sequencing of DNA inserted into the mcs.

For expression of full length human IL-1 eta protein, the entire coding region (i.e., the DNA sequence presented in SEQ ID NO:1) is amplified by polymerase chain reaction (PCR). The template employed in the PCR is the cDNA clone isolated from tonsil first strand cDNA, as described in example 1. The isolated and amplified DNA is inserted into the expression vector pDC409, to yield a construct designated pDC409-IL-1 eta.

LZ-IL-1 eta polypeptide is employed to test the ability to bind to host cells expressing recombinant or endogenous IL-1 eta receptors, as discussed above. Cells expressing IL-1 eta receptor are cultured in DMEM supplemented with 10% fetal bovine serum, penicillin, streptomycin, and glutamine. Cells are incubated with LZ-IL-1 eta (5 mg/ml) for about 1 hour. Following incubation, the cells are washed to remove unbound LZ-IL-1 eta and incubated with a biotinylated anti-LZ monoclonal antibody (5 mg/ml), and phycoerythrin-conjugated streptavidin (1:400), before analysis by fluorescence-activated cell scanning (FACS). The cytometric analysis was conducted on a FACscan (Beckton Dickinson, San Jose, Calif.).

The cells expressing IL-1 eta receptors showed significantly enhanced binding of LZ-IL-1 eta, compared to the control cells not expressing IL-1 eta receptors.

EXAMPLE 8

Expression Analysis

First strand cDNAs present in Clontech (Palo Alto, Calif.) Human Multiple Tissue cDNA Panels I (Cat. # K1420-1) and II (Cat. #K1421-1) and the Human Immune Panel (Cat. #K1426-1) were screened by PCR amplification using primers (sense: ACATCATGAACCCACAACGGGAGGCAG-CAC (SEQ ID NO:6); antisense: CTCTATCCTGGAAC-CAGCCACCCACAGC (SEQ ID NO:7)). The primers were designed to span introns so that products arising from genomic DNA and cDNA could be distinguished. In some cases, nested primers (sense: CCAAATCCTATGCTAT-TCGTGATTCTCGAC (SEQ ID NO:8); antisense: GGMTTTATTCCACAGAATCTAAGTAGAAG (SEQ ID NO:9)) were used in a second PCR reaction. The presence of an amplification product for each gene/tissue combination was determined by analysis on agarose gels stained with ethidium bromide.

Alternatively, individual cell types from human peripheral blood were isolated and stimulations were performed (Kubin et al., *Blood* 83(7):1847–55 (1994); Kubin et al., *J Exp Med* 180(1):211–22 (1994)). NK cells were incubated with IL-12 (R&D Biosystems; 1 ng/ml) for either 2 hours or 4 hours. T cells were unstimulated or stimulated with anti-CD3 (OKT-3 antibody, immobilized on plastic at 5 ng/ml) or with the combination of anti-CD3 and anti-CD28 (the anti-CD28 antibody was CD248 used in soluble form as a 1:500 dilution of ascites fluid), for 30 minutes or 4 hours. Monocytes were unstimulated, or stimulated with LPS (Sigma; 1 ug/ml) for 2 or 3 hours. B cells were unstimulated, or stimulated with the combination of 0.05% SAC and 500 ng/ml CD40L trimer (Immunex) and 5 ng/ml IL-4 (Immunex) for 3.5 or 4 hours. Dendritic cells were stimulated with LPS as for monocytes, for 2 or 4 hours. After isolation of RNA and synthesis of first strand cDNA, PCR amplifications and gel analysis were performed.

Table I demonstrates the expression of IL-1 eta in lymphoid organs. A "-" indicates that the mRNA was looked for but not found. Positive results derived by PCR analysis for a panel of first strand cDNAs (Clontech) are designated by an "A".

EXAMPLE 9

Binding Assay

This example describes a type of binding assay utilizing the inventive proteins. A recombinant expression vector containing the binding partner cDNA is constructed using methods well known in the art. CV1-EBNA-1 cells in 10 $cm^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about $4 \times 10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Auto-gamma counter. Affinity calculations (Scatchard, Ann. N.Y. Acad. Sci. 51:660, 1949) are generated on RS/1 (BBN Software, Boston, Mass.) run on a Microvax computer.

EXAMPLE 10

Activation of Signaling Molecules in Human Cells

The following describes tests and results that are carried out evaluate the induction of some of the same signaling molecules involved in stress responses as are activated by IL-1 alpha, IL-1 beta and other inflammatory cytokines.

Human IL-1 eta is transfected into COS-1 cells. Several days after the transfection, conditioned medium (containing the transiently expressed IL-1 eta) is harvested. Test cells are incubated with this conditioned medium, or alternatively with conditioned medium from COS-1 cells transfected with the empty expression vector. Approximately 10 minutes following the incubation, cell extracts are prepared from the test cells, and the presence of activated signaling molecules is assayed by the use of antibodies specific for the phosphorylated forms of IKBalpha (phosphorylation on Ser32), p38 MAP kinase (phosphorylation on Thr180 and Tyr182), and Stress-Activated Protein Kinase (SAPK/JNK) (phosphorylation on Thr183/Tyr185). The antibodies may be obtained from commercial sources, such as New England Biolabs, Beverly, Mass. These signal transduction molecules are known to be involved in a wide range of cellular responses to stimuli such as UV irradiation, endotoxin, and inflammatory cytokines including IL-1 beta. phosphorylation of one or more of these molecules indicates that IL-1 eta is involved in stress response signaling pathways.

EXAMPLE 11

Activation of Cell Surface Molecules in Human Cells

The following describes tests that are carried out to evaluate the ability of IL-1 eta to induce cell surface molecules involved in stress responses (such as those that are induced by IL-1 alpha, IL-1 beta and other inflammatory cytokines).

Human IL-1 eta is transfected into COS-1 cells. Several days after the transfection, conditioned medium (containing the transiently expressed IL-1 eta) is harvested. Human foreskin fibroblast (HFF) cells are incubated for 18 hours at 37 degrees C. with this conditioned medium diluted 1:1 with fresh 0.5% serum-containing medium, or alternatively with conditioned medium from control COS-1 cells transfected with the empty expression vector, diluted 1:1 with fresh 0.5% serum-containing medium.

Following treatment with the conditioned medium from COS-1 cells, the HFF cells are washed twice with PBS and removed from the tissue culture vessel with versene (non-trypsin reagent). Cell-surface ICAM-1 levels are measured by staining with anti-CD54-PE antibody (Pharmingen, San Diego, Calif.) on ice for one hour followed by washing and FACS-based detection. An increase in the level of cell-surface ICAM-1 indicates that IL-1 eta is involved in upregulating cell-surface molecules that are induced during stress response.

EXAMPLE 12

Modulation of Cytokine Levels by IL-1 eta

The following describes tests that are carried out to evaluate induction of cytokine secretion in dendritic cells or other cells capable of secreting cytokines.

Monocyte-derived dendritic cells (MoDC) are obtained essentially as described by Pickl et al. (J. Immunol. 157: 3850, 1996). Briefly, highly purified CD14(bright) peripheral blood monocytic cells are obtained from peripheral blood using an AutoMACS cell sorting system and anti-CD 14 magnetic microbeads (Miltenyi Biotec, Bergisch Gladbach, Germany). The monocytic cells are cultured in the presence of IL-4 and GM-CSF for seven days to yield MoDC. Similar techniques are used to obtained purified or enriched populations of other cytokine-secreting cells, for example lymphocytes or granulocytes Cells are treated for two to three days in the presence or absence of IL-1 eta at varying concentrations; lipopolysaccharide (LPS) at 10 ng/ml is used as a positive control; heat-inactivated IL-1 eta (heated at 100 degrees C. for 30 minutes) may be used as a negative control. Cells are separated from the supernatant medium by centrifugation.

The supernatant medium is analyzed for soluble cytokine levels using a suitable assay (for example, the Luminex® multi-plex cytokine assay; Luminex Corporation, Austin, Tex.). Following culture, the supernatant is harvested and assayed for several cytokines including IL-10, IL-2, IL-4, IL-6, IL-8, IL-12 (p70 heterodimer), TNF-alpha, IFN-gamma, and GM-CSF.

For analysis of the induction of cytokine mRNA, the cells are harvested and total RNA is isolated (for example, using an RNeasy® Total RNA System mini-kit, QIAGEN, Venlo, The Netherlands) and analyzed in a suitable, real-time quantitative polymerase chain reaction (PCR) analysis. Quantitative RT-PCR is performed using the ABI PRISM® 7700 Sequence Detection System (Applied Biosystems, Foster City, Calif.) and TaqMan® reagents (Applied Biosystems). An increase in the levels of one or more cytokines and/or induction of one or more cytokine mRNAs indicates that IL-1 eta upregulates cytokines that are involved in the inflammatory and/or immune response.

EXAMPLE 13

Effect of IL-1 eta on Mixed Lymphocyte Reaction (MLR)

The following describes tests carried out to evaluate the effects of IL-1 eta on TNF-alpha, IFN-gamma, and IL-10 secretion in a mixed leukocyte reaction (MLR) assay.

Briefly, highly purified CD14(bright) peripheral blood monocytic cells are obtained from peripheral blood using an AutoMACS cell sorting system and anti-CD14 magnetic microbeads (Miltenyi Biotec, Bergisch Gladbach, Germany). The monocytic cells are cultured in the presence of IL-4 and GM-CSF for seven days to yield MoDC. Purified CD3+ allogeneic T cells are obtained from freshly drawn blood using an AutoMACS cell sorting and anti-CD3 magnetic microbeads system (Miltenyi Biotec).

The allogeneic T cells are then mixed with MoDCs at a 1:10 MoDC:T ratio in quadruplicate in the presence of IL-1 eta at varying concentrations from 5 ng/ml to 200 ng/ml, or control preparations. The ensuing mixed lymphocyte reaction (MLR) is allowed to proceed for four days, and supernatants are harvested and assayed for TNF-alpha, IFN-gamma, and IL-10 using a suitable assay as described previously (for example, the Luminex® multi-plex cytokine assay, DELFIA® or ELISA substantially as described below).

EXAMPLE 14

Cytokine ELISA

The following describes an Enzyme-Linked Immunosorbent Assay (ELISA) that is useful to detect and/or quantitate secreted proteins. The Example describes an assay specific for IL-10; those of skill in the art will recognize that a similar assay could be used to detect other molecules.

ELISA plates (for example, Costar® EIA/RIA 96 well easy wash plates, Corning Incorporated Life Sciences, Acton, Mass.) are coated overnight with 100 microliter of a 2 micrograms/ml mixture of Rat-anti-huIL-10 capture antibody (BD Pharmingen, San Diego, Calif.) in binding solution (0.1M $NaH_2PO_4$, pH 9.0) at 4 degrees C. Plates are washed with wash buffer (phosphate buffered saline, or PBS, 0.5% Tween 20) four times (400 microliters/well/wash), then one time with PBS without Tween. Plates were blocked with 100 microliters of 5% non-fat dry milk in PBS for 1 hour at room temperature (RT), and then washed with wash buffer six times.

Samples and controls are added to separate wells (100 microliters/well); serial dilutions of a standard protein, recombinant HuIL-10 (BD Pharmingen) in PBS+3% BSA (starting at 10 ng/ml in 3-fold dilutions through 7 points as a standard curve, with an eighth point as a blank) is used to generate a standard curve for quantitation. The plates are incubated for one hour at RT, then washed with wash buffer six times as previously described, and incubated with biotinylated-rat-anti-HuIL-10 (BD Pharmingen; 100 microliters/well of a 200 ng/ml mixture in PBS+3% BSA) for one hour at RT. The plates are then washed six times with wash buffer as before, and streptavidin-conjugated horse radish peroxidase (SA-HRP; Zymed Laboratories, Inc., South San Francisco, Calif.; 100 microliters/well of a 1:4000 dilution in PBS+3% BSA) is added.

After incubating at RT for 30 minutes, the plates are washed for the final time as described above, and color is developed by adding 100 microliters/well of Tetramethylbenzidene (TMB) substrate (a 1:1 mixture of TMB Peroxidase Substrate: Peroxidase Solution, Kirkegaard & Perry Laboratories, Inc., Gaithersburg, Md.). The plates are incubated for 30 minutes at RT, at which time color development is stopped with 100 microliters/well of 2N $H_2SO_4$. The plates are read at 450 nm wavelength on a Molecular Dynamics (Molecular Dynamics, Sunnyvale, Calif.) plate reader, a standard curve is prepared, and the quantity of IL-10 in the samples determined by comparison to the standard curve.

EXAMPLE 15

Cytokine DELFIA

The following describes a DELFIA® (dissociated enhanced lanthanide fluoroimmunoassay; PerkinElmer LifeSciences, Wallac Oy., Turku, Finland) that is useful to detect and/or quantitate secreted proteins. The Example describes an assay specific for IL-10; those of skill in the art will recognize that a similar assay could be used to detect other molecules.

Briefly, DELFIA® plates (i.e., Costar® high binding 96-well plates, Corning Incorporated Life Sciences, Acton, Mass.) are coated with a detection (or capture) antibody (preferably a monoclonal antibody; 50 microliters of antibody solution containing 2 micrograms antibody/ml in PBS) at 4 degrees C. for 24 hours. Plates are washed with wash buffer (phosphate buffered saline, or PBS, 0.05% Tween 20) four times (300 microliters/well/wash), then used in an assay or stored.

Fifty microliters each of test supernatants and cell specific controls are added to separate wells of an antibody-coated plate; dilutions of standard proteins are used to generate a standard curve for quantitation. Test supernatants and controls are incubated in the antibody coated plate to allow binding of cytokine to the antibody. Plates are then washed and a polyclonal biotinylated detection antibody is added at a concentration of 10 nM in 50 microliters and incubated to allow binding to the captured cytokine. Plates are washed and Streptavidin-Europium (Eu) is added to the plate at a final concentration of 1 nM (0.06 micrograms/ml) in 50 microliters and incubated to allow binding to the biotinylated detection antibody. Plates are again washed and 100 microliters of enhancement solution is added to bind the Eu. The Eu in solution is then detected by time resolved fluorescence and the amount of cytokine secreted can be quantitated relative to standards which are added to each plate.

DELFIA® is amenable to full or partial automation (for example, using a Sagian Bioassay core system, Beckman Coulter, Inc., Fullerton, Calif., in combination with a plate reader such as a VICTOR2™, PerkinElmer LifeSciences), thereby rendering it useful for high-throughput testing.

EXAMPLE 16

Mouse Inflammatory Bowel Disease Models

This example describes several mouse models of inflammatory bowel disease (IBD), which includes Crohn's Disease and ulcerative colitis. Inflammatory bowel disease in animals can either occur spontaneously or can be experimentally induced. It is necessary to exercise care when selecting IBD models to study to ensure that the particular model selected appropriately represents the relevant stage of the inflammatory process under investigation. Particularly useful models of IBD include:

A. Oral Administration of Dextran Sulfate Sodium (DSS)

The DSS induction model can be used to induce either chronic or acute IBD. In the acute protocol, mice are given DSS (preferably with a molecular weight of 40 Kd; from 2% to 8%) in their drinking water for from one to eight days. The percent DSS and the duration of induction will vary depending on the strain of mouse used (for example, C3H/HeJ, C3H/He/Bir, NOD and NOD/SCID mice are highly susceptible, DBA/2, C57BL/6. BALB/c and 129/SvJ mice are moderately susceptible, with varying degrees of susceptibility relative to each other, FVB mice are moderately resistant, and NON/Ltj mice are resistant to DSS induced colitis). In the acute model, DSS is withdrawn after the induction phase. To induce chronic colitis, 2–8% DSS is administered for from 5 to seven days followed by administration of water for ten days; this cycle is repeated three to four times.

DSS-induced colitis is marked by profound inflammation in the colon of animals characterized by crypt destruction, mucosal ulceration, erosions and infiltration of lymphocytes and neutrophils into the mucosal tissue. Histopathologic changes are individually scored as 0 (no findings), 1 (minimal), 2 (mild), 3 (moderate), 4 (severe) for each of the following parameters: increased lymphocytes, increased neutrophils, ulceration, edema, crypt degeneration, and crypt regeneration. Total lesion score, crypt length and number of ulcers are also determined and used to gage severity of colitis.

B. Anti-CD3-Induced Ileitis

Mice (for example, BALB/c, C57BL/6 or MPJ mice, 6–16 weeks of age) are given a single intraperitoneal (i.p.) injection of anti-CD3epsilon antibody or control Ab (50 micrograms diluted in 500 microliters PBS, pH 7.4). In wildtype mice such as those listed above, this treatment reliably induces diarrhea without being lethal. Immunosuppressants such as cyclosporin A (CsA, 50 mg/kg) or dexamethasone (Dex, 50 mg/kg) may be given i.p. either as a single dose at the same time as anti-CD3 antibody, or daily for a total of three injections beginning at the time of anti-CD3 injection, as control molecules that downregulate any ensuing immune response and prevent or ameliorate anti-CD3-induced ileitis.

Mice are monitored for clinical signs of ileitis; mice may be sacrificed at varying time points for histopathologic analysis and/or testing by other means to evaluate apoptosis in gut tissue. For histopathology, hematoxylin and eosin (H&E) stained tissue sections of paraffin embedded intestinal specimens are graded in a blinded fashion, for example by using a quantitative histology score based on the frequency of apoptotic epithelial cells within the epithelium and the ratio of villus height to crypt length. Histological alterations of the small intestinal mucosa that may be observed include a reduced villus height, increased thickness of the crypt region, loss of Paneth cells, goblet cells and IEL in the epithelial layer and severe morphologic changes of the epithelial cells. In the villi, the enterocytes may have lost their columnar and polarized morphology and become flattened. In the crypt region, numerous apoptotic bodies may identified in the epithelium.

C. MdrKO Spontaneous Colitis

The MDR gene family was identified by an ability to confer multiple drug resistance in cell lines. Three genes have been identified in rodents (mdr1, mdr2 and mdr3), and two in humans (MDR1, MDR3). The mouse mdr1a gene encodes a 170 kDa transmembrane protein that is expressed in many tissues, including intestinal epithelial cells and subsets of lymphoid and hematopoietic cells. Its function in these cells is currently unknown, however, mice deficient in mdr1a spontaneously develop colitis. In humans, MDR1 may be associated with IBD susceptibility (Satsangi et al., *Nat. Genet.* 14:199, 1996; Brant et al., *Gastroenterology*, 118:A331, 2000), while decreased MDR1 expression has been reported in mucosal tissue from both CD and UC patients (Lawrance et al., *Hum. Mol. Genet.* 10: 445, 2001; Farrell et al., *Gastroenterology*, 118:279, 2000). Mdr1a knockout mice (MdrKO) provide a model of both acute (spontaneous) and chronic (DSS-induced) IBD, similar to that seen in humans, where IBD is generally a mixture of both chronic and acute inflammation. Acute colitis in MdrKO mice is marked by the spontaneous appearance of diarrhea and bloody stools in a subset of the mice; chronic colitis is induced by administering 3% w/v DSS for seven days in drinking water, followed by normal water.

Histopathologic changes are individually scored as 0 (no findings), 1 (minimal), 2 (mild), 3 (moderate), 4 (severe) for each of the following parameters: increased mononuclear cells, increased neutrophils, ulceration, edema, crypt degeneration, and hyperplasia.

D. *Helicobacter*-Induced Colitis

Various strains of mice with immunologic defects (i.e., IL-10$^{-/-}$ mice, recombinase-activating gene (Rag)1$^{-/-}$ mice, T-cell receptor alpha (TCRalpha)$^{-/-}$ mice) are susceptible to colitis induced by infection with *Helicobacter* spp., as described in Burich et al. (*Am J Physiol Gastrointest Liver Physiol* 281:G764, 2001). Moreover, luminal bacteria appear to be an important factor contributing to the development of IBD in mice and humans. Accordingly, introduction of *Helicobacter* spp. into immunodeficient mice also serves as an animal model of IBD humans (Burich et al. supra). In MdrKO mice, different species of *Helicobacter* may have different effects on spontaneous colitis; *H. bilis* infection induces IBD at a much earlier age, and the phenotypic appearance of *Helicobacter*-induced disease is similar, but not identical, to spontaneous IBD. In contrast, there is minimal disease in *H. hepaticus*-infected mdr1a–/– mice, and *H. hepaticus* appears to delay onset of spontaneous IBD. Accordingly, those of skill in the art can utilize a *Helicobacter*-based model of IBD substantially as described by Burich et al. supra.

EXAMPLE 17

Mouse Asthma Models

This example describes a mouse model of asthma. Mice (for example, BALB/c) are sensitized with antigen (for example, ovalbumin [OVA]) by intraperitoneal injection of the antigen in alum. Several sensitization schemes are known in the art; a preferred scheme is to inject 10 micrograms of OVA three times at one week intervals (i.e., on day –21, day —14 and day —7). The mice are then challenged with antigen either by aerosol exposure (5% OVA) or intranasal administration (0.1 mg OVA). The challenge schedule may be selected from among shorter terms (i.e., daily challenge on days 1, 2 and 3) or longer terms (i.e., weekly challenge for two to three weeks). The endpoints that are measured can include airway hyperreactivity, bronchoalveolar lavage (BAL) cell number and composition, in vitro draining lung lymph node cytokine levels, serum IgE levels, and histopathologic evaluation of lung tissue. Other animal models of asthma are known, and include the use of other animals (for example, C57BL/6 mice), sensitization schemes (for example, intranasal inoculation, use of other adjuvants or no adjuvants, etc.) and/or antigens (including peptides such as those derived from OVA or other proteinaceous antigens, ragweed extracts or other extracts such as those used in desensitization regimens, etc.).

EXAMPLE 18

Mouse Collagen Induced Arthritis Model

This example describes two mouse models of rheumatoid arthritis, both of which are induced by immunization with collagen (eg., collagen-induced arthritis or CIA). One model is dependant on tumor necrosis factor (TNF), the other is TNF-independent. Those of skill in the art recognize that other animals models of rheumatoid arthritis exist, and further that various parameters within the models can be adjusted (see, for example, Luross and Williams, *Immunology* 103:407, 2001; Schaller et al., *Nat Immunol* 2:74, 2001; Bober et al., *Arthritis Rheum* 43:2660, 2000; or Weyand, C. M. in *Rheumatology* (Oxford) 2000 June, pgs: 3–8)).

TNF-dependent CIA is induced in male, wild-type (wt) DBA/1 mice substantially as a modification of the protocol described by Courtenay, J. S. et al. (*Nature* 283:666, 1980)

by immunization of mice with Type II collagen (CII; 100–200 micrograms) in complete Freund's adjuvant (CFA), followed by a booster of CII (200 micrograms) in incomplete Freund's adjuvant (IFA) approximately three weeks later. In untreated mice, CIA manifests in the paws, with increasing severity over time.

TNF-independent CIA is induced in male TNF Receptor double knockout (TNFR DKO) mice substantially as described above. TNFR DKO mice are mice that lack functional TNF receptors (both p55 and p75), and are described in Peschon, et al. (*J. Immunol.* 160:943, 1998). Briefly, mice lacking functional p55 and p75 genes were generated in C57BL/6 background by gene targeting in embryonic stem cells. The TNFR DKO C57BL/6 mice were back-crossed on to the DBA/1 genetic background to yield mice that were homozygous for H-2q and were susceptible to development of CIA.

The severity of disease is judged by swelling and joint function of each paw, using a score from 0 to 4 (0=normal, no swelling; 1=swelling in 1 to 3 digits; 2=mild swelling in ankles, forepaws or more than three digits; 3=moderate swelling in multiple joints; 4=severe swelling with loss of function). The score for each paw is totaled for a cumulative score for each mouse; cumulative scores are totaled for the mice in each experimental group to yield a mean clinical score.

EXAMPLE 19

Mouse Experimental Allergic Encephalomyelitis Model

This example describes two mouse models of demyelinating conditions; experimental autoimmune encephalomyelitis (or EAE) is designed to duplicate the secondary, immune mediated demyelination that occurs in multiple sclerosis.

A. Myelin Oligodendrocyte Glycoprotein (MOG)-Induced EAE in C57BL/6 Mice

EAE is induced in female C57BL/6 mice substantially as described by Mendel et al. (*Eur. J. Immunol.* 25:1951–59, 1995) by immunization of mice with an antigen derived from rat myelin oligodendrocyte glycoprotein (preferably the MOG35-55 peptide described by Mendel et al., supra). Other encephalitogenic antigens may be used, including, for example, whole spinal chord homogenate, purified whole myelin, myelin basic protein, proteolipid protein, myelin associated glycoprotein, myelin-associated oligodendrocyte basic protein, or encephalitogenic peptides derived from these antigens. The disease induction protocol of Mendel et al. may be modified to include the use of a lower dose of MOG35-55 for immunization (see below), no booster immunization, and the use of RIBI® adjuvant (Corixa Corporation, Seattle Wash.) instead of complete Freund's adjuvant.

To induce EAE, groups of age and weight-matched mice are given a dose of 100 micrograms of rat MOG35-55 emulsified in 0.2 ml RIBI® adjuvant and injected subcutaneously (for example, at three sites distributed over the shaved flank of a mouse). To induce EAE with accelerated onset, mice may be given an intravenous injection 500 ng pertussis toxin (List Biological Laboratory Inc, Campbell, Calif.), administered 48 hours after administration of MOG35-55.

B. Proteolipid Protein (PLP)-Induced EAE in SJL Mice

The PLP/SJL model results in a relapsing-remitting course of disease that mimics the course often seen in MS; however, SJL mice are susceptible to anaphylaxis, and care must be given in choosing and administering therapeutic agents to avoid induction of an anaphylactic response. EAE is induced in female SJL mice substantially as described by McRae et al. et al. (*J. Neuroimmunol.* 38:229, 1992) by immunization of mice with an antigen derived from rat proteolipid protein (preferably the PLP13-151(S) peptide described by McRae et al., supra). Other encephalitogenic antigens may be used, including, for example, whole spinal chord homogenate, purified whole myelin, myelin basic protein, proteolipid protein, myelin associated glycoprotein myelin-associated oligodendrocyte basic protein, or encephalitogenic peptides derived from these antigens. The disease induction protocol of McRae et al. may be modified as described above. EAE is reliably induced in SJL/J mice actively immunized with PLP13-151(S) or another, suitable PLP-related antigen. Alternatively, EAE can be induced by adoptive transfer of PLP-specific T cells.

Administration of FIL1 antagonist(s) or control for either or both models is initiated on the day after administration of the encephalitogenic peptide (day 1) and continued through day 11. Varying injection schedules can be used to evaluate the efficacy of the FIL1 antagonist(s). Each mouse is injected intraperitoneally every other day (or according to the selected injection schedule) with 0.2 ml pyrogen-free phosphate-buffered saline (PBS) or 0.2 ml PBS containing FIL1 antagonist(s) or control. Endotoxin levels are monitored and must be less that <10 EU/mg of protein for all reagents. Mice are monitored daily for 30 to 35 days for weight loss, disease onset and severity of clinical signs of EAE by an independent observer blinded to the treatment groups.

The severity of EAE is assessed using either a standard EAE index system in which "0" is used to indicate an asymptomatic mouse and clinical scores ranging from 0.5 to 4 are used to indicate varying degrees of ascending paralysis, or a slightly modified version of the commonly used EAE scoring system. In the latter system, "0" indicates a mouse with no evidence of disease and scores of 1–5 indicate varying degrees of ascending paralysis as follows: 1, tail paralysis; 2, hind limb weakness; 3, partial hind limb paralysis; 4, complete hind limb paralysis; 5, moribund or dead. The disease protocol described above induces an acute episode of disease in control mice (peak score of 2–4) from which most recover at least partially. Thus the acute episode of disease is not lethal and mice do not reach a score of 5. The aforedescribed scale may be modified to include a score of "0.5" which is given to mice that show the earliest signs of EAE but that do not exhibit complete paralysis of the tail. Mice given a score of 0.5 exhibit some or all of the following symptoms: overnight weight loss of 1–2 grams; noticeable tremor when held up by the tail; and weakness at the distal tip of the tail.

The median day of onset of EAE is determined by Kaplan-Meier Survival analysis. Significant differences in onset between groups are assessed using a Log-Rank comparison. Fischer's exact test is used to analyze the statistical significance of differences in the incidence of EAE among the groups of mice.

EXAMPLE 20

Mouse Cuprizone-Induced Demyelinating Disease Model

This example describes a mouse model (cuprizone-induced demyelinating disease or CIDD) that is designed to mimic a type of demyelination that occurs in some cases of multiple sclerosis referred to as primary demyelination. CIDD is induced by feeding cuprizone (bis-cyclohexanone-oxaldihydrazone, a copper chelator) to mice substantially as described by Matsushima et al. (*Brain Pathol.* 11:107, 2001). At low doses of cuprizone, mature oligodendrocytes in the CNS are specifically insulted and they become unable to provide support for myelin. Demyelination occurs when the damaged myelin is stripped from the axons by microglia.

Some advantages of the CIDD model are that it reproducibly results in massive demyelination in a large area of the mouse brain and it is reversible if cuprizone is removed from the diet. The model appears well suited for profiling gene expression during various stages of demyelination and remyelination. The model has been established in C57BL/6 mice, so it is also suitable for use in KO (knockout) or Tg (transgenic) mice with the B6 background. However, there are no obvious clinical signs associated with the demyelinating process, so analysis must be done by histology.

What is the claimed is:

1. An isolated polynucleotide comprising a polynucleotide that is at least 98% identical to SEQ ID NO:1 and that encodes a polypeptide that activates MAP kinase.

2. An expression vector comprising the polynucleotide of claim 1.

3. A host cell comprising the expression vector of claim 2.

4. A process for preparing a polypeptide comprising culturing a host cell of claim 3 under conditions that promotes expression of the polypeptide.

* * * * *

UNITED STATES PATENT AND TRADEMARK OFFICE
CERTIFICATE OF CORRECTION

PATENT NO.         : 7,223,565 B2
APPLICATION NO.    : 10/843189
DATED              : May 29, 2007
INVENTOR(S)        : John E. Sims and Blair R. Renshaw It is certified that error appears in the above-identified patent and that said Letters Patent is hereby corrected as shown below:

Title Page, Item 63, Line 2: Insert after Oct. 11, 2001, -- now Pat. No. 6,753,166, --

Title Page, Item 63, Line 4: Delete ", now Pat. No. 6,753,166"

Column 12, Line 32: Change "region" to -- regions --.

Column 13, Line 46: Add a period at the end of the sentence after "1993)".

Column 17, Line 9: Change "Feigner" to -- Felgner --

Column 26, Lines 15: Change "can hybridizing" to -- hybridizing --

Column 33, Line 31: Change "Behcet's" to -- Behçet's --

Column 34, Line 16: Change "fragment" to -- fragments --

Column 34, Line 23: Change "amino acids" to -- amino acid --

Column 36, Line 50: Change "Linbro/Fitertek" to -- Linbro/Titertek --

Column 38, Line 44: Change the punctuation at the end of the sentence from ".).)." to -- .). --

Column 40, Line 5: At the beginning of the line, change "GGM" to -- GGA --

Column 41, Line 35: Change "phosphorylation" to -- Phosphorylation --.

Column 42, Line 16: Change "obtained" to -- obtain --

Column 42, Line 18: Add a "period" after "granulocytes".

Column 42, Line 47: Change "Lvmphocyte" to -- Lymphocyte --

Column 44, Line 53: Change "C3He/BIR" to -- C3HeJBir --

Column 46, Line 64: Change "pgs:3-8))." to -- pgs:3-8). --

Column 48, Line 5: Change "McRae et al.et al." to -- McRae et al. --

UNITED STATES PATENT AND TRADEMARK OFFICE
CERTIFICATE OF CORRECTION

PATENT NO. : 7,223,565 B2
APPLICATION NO. : 10/843189
DATED : May 29, 2007
INVENTOR(S) : John E. Sims and Blair R. Renshaw It is certified that error appears in the above-identified patent and that said Letters Patent is hereby corrected as shown below:

Column 48, Line 28: Change "less that < 10 EU/mg" to -- less than 10 EU/mg --

Column 53, Line 39: Change "What is the claimed is:" to -- What is claimed is: --

Column 54, Line 39: Change "A host" to -- An isolated host --

Signed and Sealed this

Sixth Day of May, 2008

JON W. DUDAS
*Director of the United States Patent and Trademark Office*

SEQUENCE LISTING

<160> NUMBER OF SEQ ID NOS: 9

<210> SEQ ID NO 1
<211> LENGTH: 585
<212> TYPE: DNA
<213> ORGANISM: Homo sapiens
<220> FEATURE:
<221> NAME/KEY: CDS
<222> LOCATION: (112)..(585)

<400> SEQUENCE: 1

```
ggcacgaggt tcctccccac tctgtctttc tcacctctcc ttcacttttc ctagcctcct        60
caccaccatc tgatctatct tgttctcttc acaaaaggct ctgaagacat c atg aac       117
                                                          Met Asn
                                                            1 cca caa cgg gag gca gca ccc aaa tcc tat gct att cgt gat tct cga        165
Pro Gln Arg Glu Ala Ala Pro Lys Ser Tyr Ala Ile Arg Asp Ser Arg
         5                  10                  15 cag atg gtg tgg gtc ctg agt gga aat tct tta ata gca gct cct ctt        213
Gln Met Val Trp Val Leu Ser Gly Asn Ser Leu Ile Ala Ala Pro Leu
 20                  25                  30 agc cgc agc att aag cct gtc act ctt cat tta ata gcc tgt aga gac        261
Ser Arg Ser Ile Lys Pro Val Thr Leu His Leu Ile Ala Cys Arg Asp
 35                  40                  45                  50 aca gaa ttc agt gac aag gaa aag ggt aat atg gtt tac ctg gga atc        309
Thr Glu Phe Ser Asp Lys Glu Lys Gly Asn Met Val Tyr Leu Gly Ile
                 55                  60                  65 aag gga aaa gat ctc tgt ctc ttc tgt gca gaa att cag ggc aag cct        357
Lys Gly Lys Asp Leu Cys Leu Phe Cys Ala Glu Ile Gln Gly Lys Pro
             70                  75                  80 act ttg cag ctt aag gaa aaa aat atc atg gac ctg tat gtg gag aag        405
Thr Leu Gln Leu Lys Glu Lys Asn Ile Met Asp Leu Tyr Val Glu Lys
         85                  90                  95 aaa gca cag aag ccc ttt ctc ttt ttc cac aat aaa gaa ggc tcc act        453
Lys Ala Gln Lys Pro Phe Leu Phe Phe His Asn Lys Glu Gly Ser Thr
    100                 105                 110 tct gtc ttt cag tca gtc tct tac cct ggc tgg ttc ata gcc acc tcc        501
Ser Val Phe Gln Ser Val Ser Tyr Pro Gly Trp Phe Ile Ala Thr Ser
115                 120                 125                 130 acc aca tca gga cag ccc atc ttt ctc acc aag gag aga ggc ata act        549
Thr Thr Ser Gly Gln Pro Ile Phe Leu Thr Lys Glu Arg Gly Ile Thr
                135                 140                 145 aat aac act aac ttc tac tta gat tct gtg gaa taa                         585
Asn Asn Thr Asn Phe Tyr Leu Asp Ser Val Glu
                150                 155
```

<210> SEQ ID NO 2
<211> LENGTH: 157

```
<212> TYPE: PRT
<213> ORGANISM: Homo sapiens

<400> SEQUENCE: 2

Met Asn Pro Gln Arg Glu Ala Ala Pro Lys Ser Tyr Ala Ile Arg Asp
1               5                   10                  15

Ser Arg Gln Met Val Trp Val Leu Ser Gly Asn Ser Leu Ile Ala Ala
            20                  25                  30

Pro Leu Ser Arg Ser Ile Lys Pro Val Thr Leu His Leu Ile Ala Cys
        35                  40                  45

Arg Asp Thr Glu Phe Ser Asp Lys Glu Lys Gly Asn Met Val Tyr Leu
    50                  55                  60

Gly Ile Lys Gly Lys Asp Leu Cys Leu Phe Cys Ala Glu Ile Gln Gly
65                  70                  75                  80

Lys Pro Thr Leu Gln Leu Lys Glu Lys Asn Ile Met Asp Leu Tyr Val
            85                  90                  95

Glu Lys Lys Ala Gln Lys Pro Phe Leu Phe Phe His Asn Lys Glu Gly
            100                 105                 110

Ser Thr Ser Val Phe Gln Ser Val Ser Tyr Pro Gly Trp Phe Ile Ala
            115                 120                 125

Thr Ser Thr Ser Gly Gln Pro Ile Phe Leu Thr Lys Glu Arg Gly
        130                 135                 140

Ile Thr Asn Asn Thr Asn Phe Tyr Leu Asp Ser Val Glu
145                 150                 155

<210> SEQ ID NO 3
<211> LENGTH: 8
<212> TYPE: PRT
<213> ORGANISM: Artificial
<220> FEATURE:
<223> OTHER INFORMATION: FLAG

<400> SEQUENCE: 3

Asp Tyr Lys Asp Asp Asp Asp Lys
1               5

<210> SEQ ID NO 4
<211> LENGTH: 27
<212> TYPE: PRT
<213> ORGANISM: artificial sequence
<220> FEATURE:
<223> OTHER INFORMATION: lung SPD leucine zipper peptide

<400> SEQUENCE: 4

Pro Asp Val Ala Ser Leu Arg Gln Gln Val Glu Ala Leu Gln Gly Gln
1               5                   10                  15

Val Gln His Leu Gln Ala Ala Phe Ser Gln Tyr
            20                  25

<210> SEQ ID NO 5
<211> LENGTH: 33
<212> TYPE: PRT
<213> ORGANISM: artificial sequence
<220> FEATURE:
<223> OTHER INFORMATION: leucine zipper

<400> SEQUENCE: 5

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30
```

```
Arg

<210> SEQ ID NO 6
<211> LENGTH: 30
<212> TYPE: DNA
<213> ORGANISM: Homo sapiens

<400> SEQUENCE: 6
acatcatgaa cccacaacgg gaggcagcac                                      30

<210> SEQ ID NO 7
<211> LENGTH: 28
<212> TYPE: DNA
<213> ORGANISM: Homo sapiens

<400> SEQUENCE: 7
ctctatcctg gaaccagcca cccacagc                                        28

<210> SEQ ID NO 8
<211> LENGTH: 30
<212> TYPE: DNA
<213> ORGANISM: Homo sapiens

<400> SEQUENCE: 8
ccaaatccta tgctattcgt gattctcgac                                      30

<210> SEQ ID NO 9
<211> LENGTH: 29
<212> TYPE: DNA
<213> ORGANISM: Homo sapiens

<400> SEQUENCE: 9
ggatttattc cacagaatct aagtagaag                                       29
```